United States Patent [19]

Sneider

[11] 4,254,769

[45] Mar. 10, 1981

[54] COLLAPSIBLE CONTAINER APPARATUS WITH AIR VENT AND SHUT-OFF VALVE

[76] Inventor: Vincent R. Sneider, 3422 Hallcrest Dr., Atlanta, Ga. 30319

[21] Appl. No.: 115,130

[22] Filed: Jan. 24, 1980

[51] Int. Cl.³ .............................................. A61M 3/00
[52] U.S. Cl. .................................................... 128/227
[58] Field of Search ....... 128/227, 251, 272, DIG. 23, 128/247

[56] References Cited

U.S. PATENT DOCUMENTS

| | | | |
|---|---|---|---|
| 2,044,911 | 6/1936 | Miller | 128/227 |
| 2,515,470 | 7/1950 | Prytz | 128/227 |
| 3,481,334 | 12/1969 | Diskin et al. | 128/227 X |
| 3,993,070 | 11/1976 | Sneider | 128/251 |

Primary Examiner—John D. Yasko
Attorney, Agent, or Firm—Ralph R. Roberts

[57] ABSTRACT

The container of this invention is accordion-pleated and is provided in a collapsed condition for normal shipment. Just prior to use, one end of the container is opened and filled with water. Powder or a tablet is usually provided in the container for mixing with water. The cover of the closure has an air valve which includes a ball, slightly spring loaded, and a closure valve contained in a remotely carried nozzle attachment. This valve is manipulated to an open condition and is closed by pressure on the extending wing or flanged portions of the valve. The closure end of the container is preferably connected by flexible tubing to the valve which is also secured to the nozzle.

10 Claims, 4 Drawing Figures

COLLAPSIBLE CONTAINER APPARATUS WITH AIR VENT AND SHUT-OFF VALVE

BACKGROUND OF THE INVENTION

1. Field of the Invention

This invention pertains to the field of art found generally in the Class entitled, "Surgery" (Class 128) and more particularly in the subclass entitled, "douches" and even more particularly in the subclass of "Vaginal douches" (Subclass 232).

2. Description of the Prior Art

Disposable douches and similar syringe devices are well known in the prior art and several have been shown and described. Included in these are disposable syringes, or douche devices having pre-mixed liquid contents. In the present invention it is contemplated that an accordion-type container includes a powder which can be readily mixed with water to make an antiseptic solution. The container apparatus of this invention may be inexpensive and disposable or can be a travelling component that is used over and over with the antiseptic portion being a tablet or powder which is mixed with water from a ready source of supply.

SUMMARY OF THE INVENTION

This invention may be summarized, at least in part, with reference to its objects.

It is an object of this invention to provide, and it does provide, an improved douche, enema container or the like and having a construction which allows for ready mixing at the point of use. This container includes a hook which may be hung on a rod so that gravity force may be applied at the nozzle. The cap closure for the container or bag is readily removable and has an automatic check valve which allows air to enter the bag so that intermixed fluid in the bag may be readily discharged when the cut-off valve is manipulated to an open condition.

Another object of this invention is to provide a collapsible construction of a container and a remote manipulative valve which is located at the nozzle to close and open the flow of water or fluid in the tubing from the container to the nozzle.

A further object of the invention provides a tubing shut-off which is disposed at the end of a flexible tube in conjunction with a thread attached nozzle. This shut off is adapted for closure to the flow of fluid when the flanged portions are moved away from each other and with a natural action or pressure this valve is caused to open to provide a flow of fluid from the container through the tubing and to the nozzle.

In brief, this invention provides a collapsible container and syringe which includes a hanger on the closed end by which the container may be suspended for use. At the other end said container has an opening for the addition of water or other fluid into the container. A cover having a ball-type vent is provided so that air can enter the container when its brought to a condition of reduced pressure.

In addition to the above summary the following disclosure is detailed to insure adequacy and aid in understanding of the invention. This disclosure, however, is not intended to cover each new inventive concept no matter how it may later be disguised by variations in form or additions of further improvements. For this reason there has been chosen a specific embodiment of a collapsible container and valve as adopted for use as a douche or syringe and showing a preferred means for construction and use. This specific embodiment has been chosen for the purposes of illustration and description as shown in the accompanying drawing.

BRIEF DESCRIPTION OF THE DRAWING

In the following description and in the claims various details are identified by specific names for convenience. These names are intended to be generic in their application. Corresponding reference characters refer to like members throughout the several figures of the drawings.

The drawings accompanying, and forming part of, this specification disclose details of construction for the purpose of explanation but structural details may be modified without departure from the concept and principles of the invention and the invention may be incorporated other structural forms than shown.

DESCRIPTION OF THE PREFERRED EMBODIMENT

Figure 1:
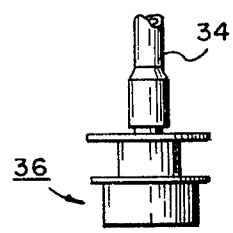
FIG. 1 represents a side view, partly in section, showing the collapsible container and in particular the connecting tubing portion broken away.
Figure 4:
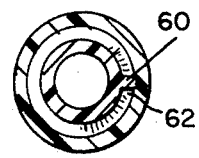
FIG. 4 represents a sectional view of the valve as taken on the line 4—4 of FIG. 2 and looking in the direction of the arrows.

In FIG. 1 there is shown a collapsible container 10 which has a plural pleated bag which is adapted to collapse upon itself.

Figure 2:
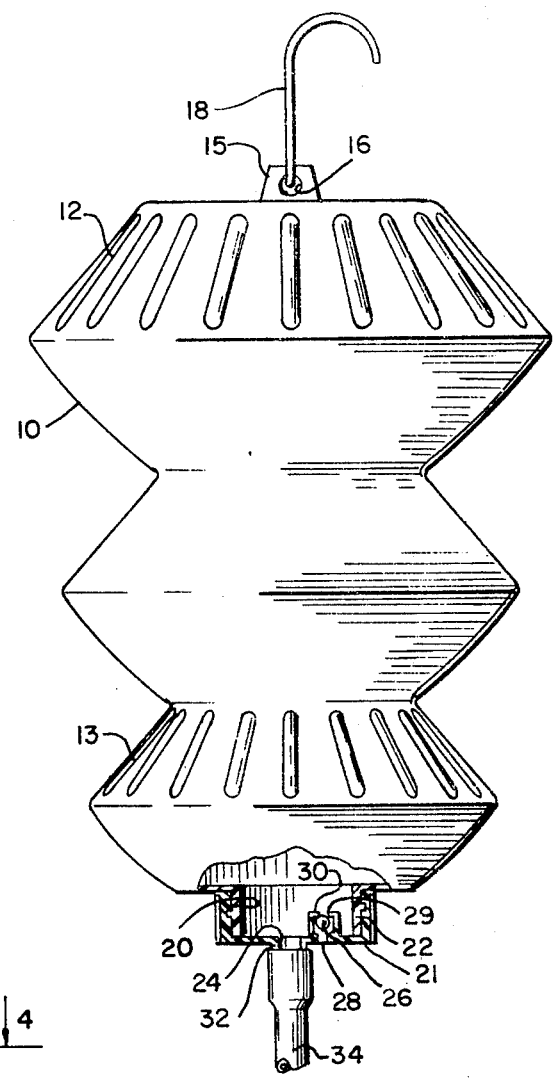
FIG. 2 represents a side view in an enlarged scale and in section of a remote control valve operable in conjunction with a typical discharge nozzle.
Figure 2:
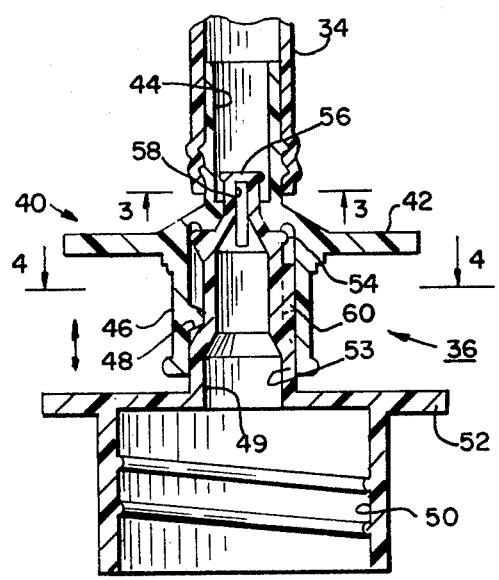

This container has upper and lower rib portions 12 and 13 providing ease of manipulation and grasping of the accordion pleated container to draw it into an expanded condition. At the upper end or closed end of the container there is provided a protruding tab 15 which has a hole 16 formed therein. In this hole is mounted a hook 18, normally of wire. The open or lower end of the container 10 has formed thereon a threaded collar 20. Secured to the collar 20 by threads is a closure member 21 having a mating portion 22. In this closure member is provided a conduit 24 in which is carried in passageway 29, a ball 26. This ball may be lightly spring loaded to close an aperture 28 and this aperture provides a passageway 29 for the flow of air into the container to reduce negative pressure as it develops as and with the withdrawal of fluid from the container. The inner end 30 of this passageway is open to the interior of the container 10. Inward movement of this ball allows air to enter and to flow through this passageway 29 into the interior of the container. This conduit 24 includes a protruding, tubular discharge portion 32 on which is secured one end of a flexible hose 34. This hose, at its other end, is secured to a shut-off discharge valve generally identified as 36. This valve is shown more fully and in detail in FIG. 2.

SHUT-OFF VALVE AS SHOWN IN FIG. 2

The shut-off valve 36 includes an outer and upper portion 40 which includes an outer flange 42 and an upwardly extending tubular portion 44. This outer body portion also includes a downwardly extending skirt 46 having a stop and/or shoulder portion 48 which is internally contoured to slide on and engage a tapered portion of the lower and internal portion 49 of the valve 36. This lower and interior portion of the valve includes a threaded portion 50 below a protruding flange 52. Centrally formed on this lower member is a tubular portion 53 which extends upwardly to a shoulder 54. An upper end 55 of the inner portion of the valve is closed by and with the disk member 56. Immediately below upper end 55 the stem portion has a three fold passageway 58 which conducts fluid from the flexible hose 34 into the interior of the valve. It is to be noted that a key portion 60 may be provided on this upper end portion 55 so that the flange is not turnable on the lower and interior portion 49. This key maintains said portions in the desired orientation. On the lower portion is formed a keyway 62. This key 60 and keyway 62, when used, insure that no turning occurs.

Figure 3:
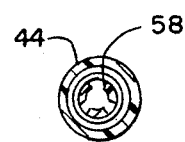
FIG. 3 represents a sectional view of the valve as taken on the line 3—3 of FIG. 2 and looking in the direction of the arrows.

In FIG. 3 the upper portion of the valve is shown with a three-fold passageway 58. The upper stem portion 65 provides the interior walls of the shut-off valve 36. The outer wall portion 64 has a sliding relationship with the upper portion of the valve on and to the lower portion.

USE AND OPERATION

Prior to use it is contemplated that the container 10 is in a substantially flat or closed condition. A powder or tablet may be placed within the collapsed container and a flexible seal may be provided over the threaded collar 20. The container 10 is opened to its expanded condition and filled with fluid. Said fluid flows through the threaded collar opening 20 into the interior of the container. The closure member 21 is screwed in place to provide a closing seal of the now filled container. Valve 36 is now positioned in a closed condition with the outer flange member 42 moved upwardly to bring disk member 56 against the terminal end of the lower portion of the valve. The hook 18 may be grasped for ease of manipulation and said container is then agitated. After mixing of the components, the nozzle, which is not shown but is of conventional design, may be screwed into the threaded portion 50 of the valve 36 and then said nozzle may be inserted for use. The valve is opened to the condition of FIG. 2 by forcing or moving the outer flange portion 42 towards the protruding flange 52 and into the position of FIG. 2. In an open condition this valve provides for the movement of fluid from the container down the flexible hose 34 through and past the shut-off valve member 36, into the passageway 58 and into the interior of the lower valve portion from which it passes through to the nozzle. Manipulation again provides a closing of the valve. Disassembly, cleaning and storage of the syringe apparatus is conventional and according to the desire of the user.

It is to be noted that the vent may be closed by a ball moved only by gravity. Other vent closing means can also be provided. The spring assist for a ball or the like may be either a coil, leaf or like member or may be a rubber plug providing a one-way action. The nozzle may be secured to the valve as by threads or by a tapered mounting. The valve may include a key and keyway if desired. The valve may use means other than a disk to close the passageway to a flow of fluid.

Terms such as "left", "right", "up", "down", "bottom", "top", "front", "back", "in", "out", and the like are applicable to the embodiment shown and described in conjunction with the drawing. These terms are merely for the purposes of description and do not necessarily apply to the position in which the collapsible container may be constructed or used.

While a particular embodiment of the collapsible container has been shown and described it is to be understood the invention is not limited thereto since modifications may be made within the scope of the accompanying claims and protection is sought to the broadest extent the prior art allows.

What is claimed is:

1. A collapsible container for mixing and feeding fluid to a syringe for vaginal douches, enemas and the like, and as a combination including: (a) a collapsible container having a closed end and an open end; (b) an access opening formed in said open end; (c) a closure member adapted for the removably securing of said closure member to said access opening of the container, said closure member having a discharge means for carrying fluid through said closure member; (d) an automatically closeable vent means provided in said closure member, this vent adapted to admit air to the interior of the container when the container is brought to and into a condition of reduced pressure and to close said vent to fluid flow when the container approaches atmospheric pressure; (e) a flexible conductor secured at one end to the discharge carrier means provided on and by the closure member and at its other end said flexible conductor is removably secured to a selectively closeable valve; (f) this valve having a longitudinally movable outer tubular member having means for securing said flexible conductor to the valve so as to carry fluid to the interior of said valve; (g) a shut-off arranged in said valve and forming a portion of an inner member; (h) flange means on the movable valve components and providing manipulative means for opening and closing the valve to a flow of fluid; (i) means to limit the apart and together position of this valve, and (j) means for securing a nozzle on the discharge end of the valve.

2. A collapsible container as in claim 1 in which the vent in the closure member is a ball movable in a passageway and at one limit the ball closes the passageway and when displaced from said limit the passageway is opened to admit air so as to enter the container when under the influence of reduced pressure.

3. A collapsible container as in claim 2 in which there is a small biasing influence urging the ball to a closed condition.

4. A collapsible container as in claim 1 in which the container is an accordian pleated container.

5. A collapsible container as in claim 4 in which the container has its closed end formed with a tab in which a hole is provided and in this hole is secured a hook.

6. A collapsible container as in claim 1 in which the selectively closeable valve has mating inner and outer tubular portions on and to which there is provided outwardly extending flanges which are manipulated away from each other to close the shut-off valve and are moved toward each other to open said valve.

7. A collapsible container as in claim 6 in which the lower portion of the valve has a closure disk at one end thereof and immediately below this disk is formed a plurality of apertures which provide fluid passageways when and while the disk is moved from its closure condition.

8. A collapsible container as in claim 1 in which the shut-off valve includes a complimentary key and keyway means.

9. A collapsible container as in claim 8 in which the valve includes slidable inner and outer members with the key and keyway carried in a concealed manner.

10. A collapsible container as in claim 1 in which the shut-off valve includes tubular portions that are slidable along each other and the members are formed with complimentary shoulders to limit the apart and together position of the valve.

* * * * *